US009462935B2

(12) United States Patent
Takazawa et al.

(10) Patent No.: US 9,462,935 B2
(45) Date of Patent: Oct. 11, 2016

(54) ENDOSCOPE CLEANING/DISINFECTING APPARATUS

(71) Applicant: OLYMPUS CORPORATION, Tokyo (JP)

(72) Inventors: Masataka Takazawa, Hachioiji (JP); Hiroo Takada, Hachioiji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/855,790

(22) Filed: Sep. 16, 2015

(65) Prior Publication Data
US 2016/0000310 A1    Jan. 7, 2016

Related U.S. Application Data

(63) Continuation of application No. PCT/JP2014/074913, filed on Sep. 19, 2014.

(30) Foreign Application Priority Data

Jan. 8, 2014 (JP) ................................. 2014-001893

(51) Int. Cl.
*A61L 2/18*     (2006.01)
*A61B 1/12*     (2006.01)
*B08B 3/08*     (2006.01)
*G02B 23/24*    (2006.01)

(52) U.S. Cl.
CPC .................. *A61B 1/123* (2013.01); *A61L 2/18* (2013.01); *B08B 3/08* (2013.01); *G02B 23/2476* (2013.01)

(58) Field of Classification Search
CPC ....... A61L 2/18; A61L 2202/24; A61L 2/24; A61L 2/26; A61B 1/123
USPC ...... 134/99.2, 94.1, 56 R, 56 D, 57 D, 58 D, 134/93, 18, 200, 26, 29, 99.1, 92; 422/292, 422/300, 28, 16, 905; 222/129, 651, 135, 222/173, 454, 83.5; 68/17 R, 12.18, 207; 215/379, 395, 386, 43

See application file for complete search history.

(56) References Cited

U.S. PATENT DOCUMENTS

| 6,656,438 B1* | 12/2003 | Kinoshita | A61L 2/26 215/386 |
| 2008/0115814 A1* | 5/2008 | Hasegawa | A61B 1/123 134/56 R |
| 2008/0118420 A1* | 5/2008 | Kotani | A61L 2/18 422/300 |
| 2012/0125385 A1 | 5/2012 | Komiya et al. | |
| 2012/0125878 A1 | 5/2012 | Komiya et al. | |
| 2013/0118537 A1* | 5/2013 | Komiya | A61B 1/121 134/166 C |

FOREIGN PATENT DOCUMENTS

| EP | 2457595 A1 | 5/2012 |
| EP | 2508121 A1 | 10/2012 |
| JP | 2010-057751 A | 3/2010 |
| JP | 2010-240038 A | 10/2010 |
| JP | 2012-110475 A | 6/2012 |
| JP | 2013-165803 A | 8/2013 |
| JP | 2013-165805 A | 8/2013 |
| WO | WO 2012/070267 A1 | 5/2012 |

* cited by examiner

*Primary Examiner* — David Cormier
*Assistant Examiner* — Thomas Bucci
(74) *Attorney, Agent, or Firm* — Scully, Scott, Murphy & Presser, PC

(57) ABSTRACT

A chemical bottle is inclined by a bottle push-up mechanism, and a chemical solution is gravitationally injected into a chemical tank from a chemical supply tube line. When a chemical tray is drawn out after completion of chemical injection, the bottle push-up mechanism returns to a planar initial state. In connection with this, the chemical bottle returns to an original set position in which the chemical bottle is in a horizontal state or a plug section faces upward with respect to a gravity direction. This prevents the chemical solution remaining in the chemical bottle from flowing to an outside by gravity.

5 Claims, 11 Drawing Sheets

ENDOSCOPE CLEANING/DISINFECTING APPARATUS

CROSS REFERENCE TO RELATED APPLICATION

This application is a continuation application of PCT/JP2014/074913 filed on Sep. 19, 2014 and claims benefit of Japanese Application No. 2014-001893 filed in Japan on Jan. 8, 2014, the entire contents of which are incorporated herein by this reference.

BACKGROUND OF THE INVENTION

1. Field of the Invention

The present invention relates to an endoscope cleaning/disinfecting apparatus that cleans/disinfects an endoscope.

2. Description of the Related Art

In recent years, endoscopes are widely used in a medical field and in an industrial field. An endoscope used in the medical field can observe organs in a body by inserting an elongated insertion section into the body. The endoscope can also perform various treatments by using a treatment instrument included in the endoscope, which is inserted into an insertion channel of the treatment instrument as necessary.

The endoscope in the medical field is used while being inserted into the body for a purpose of examination and treatment in particular. Therefore, the endoscope after being used needs cleaning/disinfecting for reuse. It is commonly known that the used endoscope is cleaned/disinfected by hand washing as well as by an automatic endoscope cleaning/disinfecting apparatus.

A disinfecting chemical solution for use in the endoscope cleaning/disinfecting apparatus is stored in a sealed chemical bottle. The chemical bottle is set, and the chemical solution therein is injected into the endoscope cleaning/disinfecting apparatus.

Japanese Patent Application Laid-Open Publication No. 2013-165803 discloses a liquid supply mechanism in which guide rails for guiding a bottle conveyance tray, on which a disinfecting solution bottle is mounted, is bent and the disinfecting solution bottle is caused to advance along a track of the guide rails, so that an opening of the bottle faces upward at a set position and faces downward at an opening position by a cutting section.

SUMMARY OF THE INVENTION

An endoscope cleaning/disinfecting apparatus according to one implementation aspect of the present invention is an endoscope cleaning/disinfecting apparatus for cleaning/disinfecting an endoscope, including: a bottle insertion passage having an opening section on a wall surface of an apparatus body and for introducing a chemical bottle with a chemical solution enclosed therein; an unsealing section placed in the bottle insertion passage for unsealing a chemical discharge section of the chemical bottle to form a chemical discharge port in the chemical bottle; a bottle set section placed movably back and forth inside the bottle insertion passage for housing the chemical bottle so that the chemical discharge section faces upward or sideward with respect to a gravity direction; a guide section placed in the bottle insertion passage for restricting an advancing direction of the bottle set section so that the bottle set section moves linearly back and forth in a portion between the first position and the second position, assuming that a position of the bottle set section for laying the chemical bottle on the bottle set section and for extracting the chemical bottle from the bottle set section is defined as a first position, and a position of the bottle set section for unsealing the chemical bottle with the unsealing section is defined as the second position; a first push-up section fixed to the bottle insertion passage; and a second push-up section placed in the bottle set section for transferring force to the chemical bottle to push up a first end portion of the chemical bottle so that the chemical discharge port faces downward in the gravity direction, the force being received upon collision with the first push-up section when the bottle set section is caused to advance from the first position to the second position.

DETAILED DESCRIPTION OF THE PREFERRED EMBODIMENTS

Embodiments of the present invention will be described hereinbelow with reference to the drawings.

First Embodiment

Figure 1:
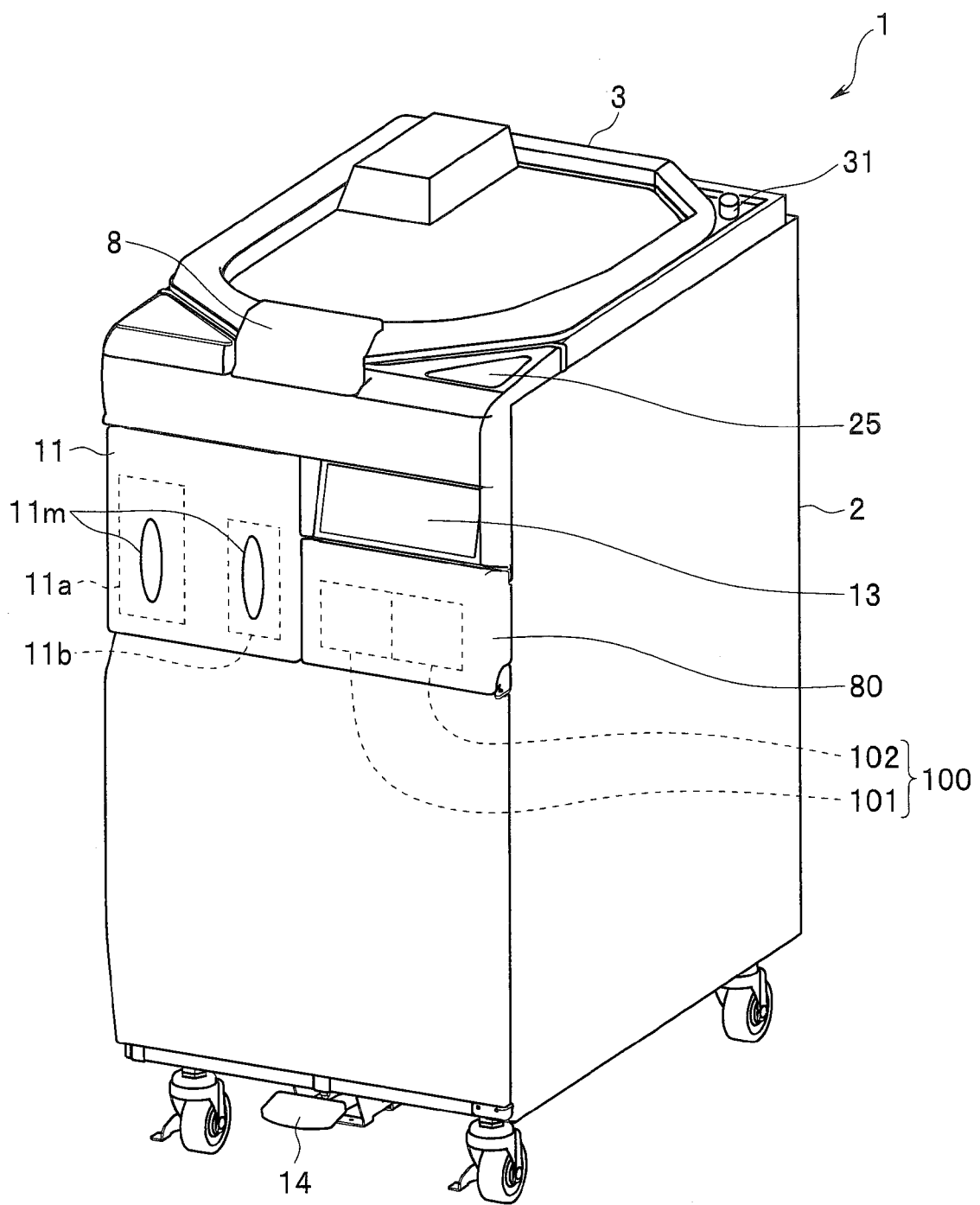
FIG. 1 is a perspective view illustrating one example of an external appearance of an endoscope cleaning/disinfecting apparatus in a first embodiment of the present invention.

In FIG. 1, a reference numeral 1 designates an endoscope cleaning/disinfecting apparatus for automatically cleaning/disinfecting an endoscope. The endoscope cleaning/disinfecting apparatus 1 includes an apparatus body 2, and a top cover 3 openably and closably connected to an upper portion of the apparatus body 2 via a hinge which is not illustrated, for example. While the top cover 3 is closed to cover the apparatus body 2, the apparatus body 2 and the top cover 3 are configured to be fixed by, for example, a latch 8 arranged at a position where the apparatus body 2 and the top cover 3 face each other.

On an upper portion of a left half portion in FIG. 1 that is on a front surface of the apparatus body 2 in FIG. 1 accessed by an operator of the apparatus body 2, a detergent/alcohol tray 11 is arranged to be freely drawn out to a front side of the apparatus body 2. The detergent/alcohol tray 11 houses a detergent tank 11a storing a cleaning solution for use in cleaning the endoscope, and an alcohol tank 11b storing an alcohol for use in drying the cleaned/disinfected endoscope. Since the detergent/alcohol tray 11 is freely drawn out, each of the tanks 11a and 11b can be supplemented with specified liquids.

Note that the detergent/alcohol tray 11 is provided with two window sections 11m. The window sections 11m enable the operator to confirm remaining amounts of the cleaning solution and the alcohol injected to each of the tanks 11a and 11b. The cleaning solution is a concentrated detergent diluted to a specified concentration with tap water which is subjected to filtration processing with an unillustrated supply water filter.

On an upper portion of a right half portion in FIG. 1 that is on the front surface of the apparatus body 2, a chemical tray 81, which is housed in a later-described chemical bottle insertion passage 80, is arranged to be drawn out freely toward the front side of the apparatus body 2. A chemical bottle 100 that encloses a chemical solution for use in disinfecting the endoscope, such as a disinfecting solution and a buffer solution for the disinfecting solution, is attached to and housed in the chemical tray 81. Since the chemical tray 81 is freely drawn out, the chemical bottle 100 can be replaced.

For example, the chemical bottle 100 is constituted of two chemical bottles 101 and 102. These chemical bottles 101 and 102 are integrally attached to and housed in the chemical tray 81. Note that the chemical bottle 100 may be constituted of one bottle, or three or more bottles. Examples of the chemical solution enclosed in the chemical bottle 100 include a disinfecting solution, such as peracetic acid.

A sub operation panel 13 is arranged on an upper portion of the chemical tray 81 that is on the front surface of the apparatus body 2. The sub operation panel 13 includes a display of a cleaning/disinfecting time period, indication buttons for warming the disinfecting solution, and the like. A pedal switch 14 is arranged on a lower portion of the apparatus body 2. The pedal switch 14 is to open the top cover 3, which is closed to cover the upper portion of the apparatus body 2, toward an upper side of the apparatus body 2 in response to a stepping operation by the operator.

A main operation panel 25 is also provided on an upper surface of the apparatus body 2, which is in a vicinity of an end portion on a front surface side accessed by the operator, for example. On the main operation panel 25, setting switches are arranged, including a cleaning and disinfecting operation start switch and a cleaning and disinfecting mode selection switch of the apparatus body 2.

A water supply hose connection port 31 to be connected to a water supply hose 31a (see FIG. 2), which is connected to a tap water faucet 5 for supplying tap water to the apparatus body 2, is arranged on the upper surface of the apparatus body 2 on a rear side opposite to the front surface accessed by the operator. Note that the water supply hose connection port 31 may be equipped with a mesh filter that filters the tap water.

Next, an internal configuration of the endoscope cleaning/disinfecting apparatus 1 in the present embodiment will be described with reference to FIG. 2.

Figure 2:
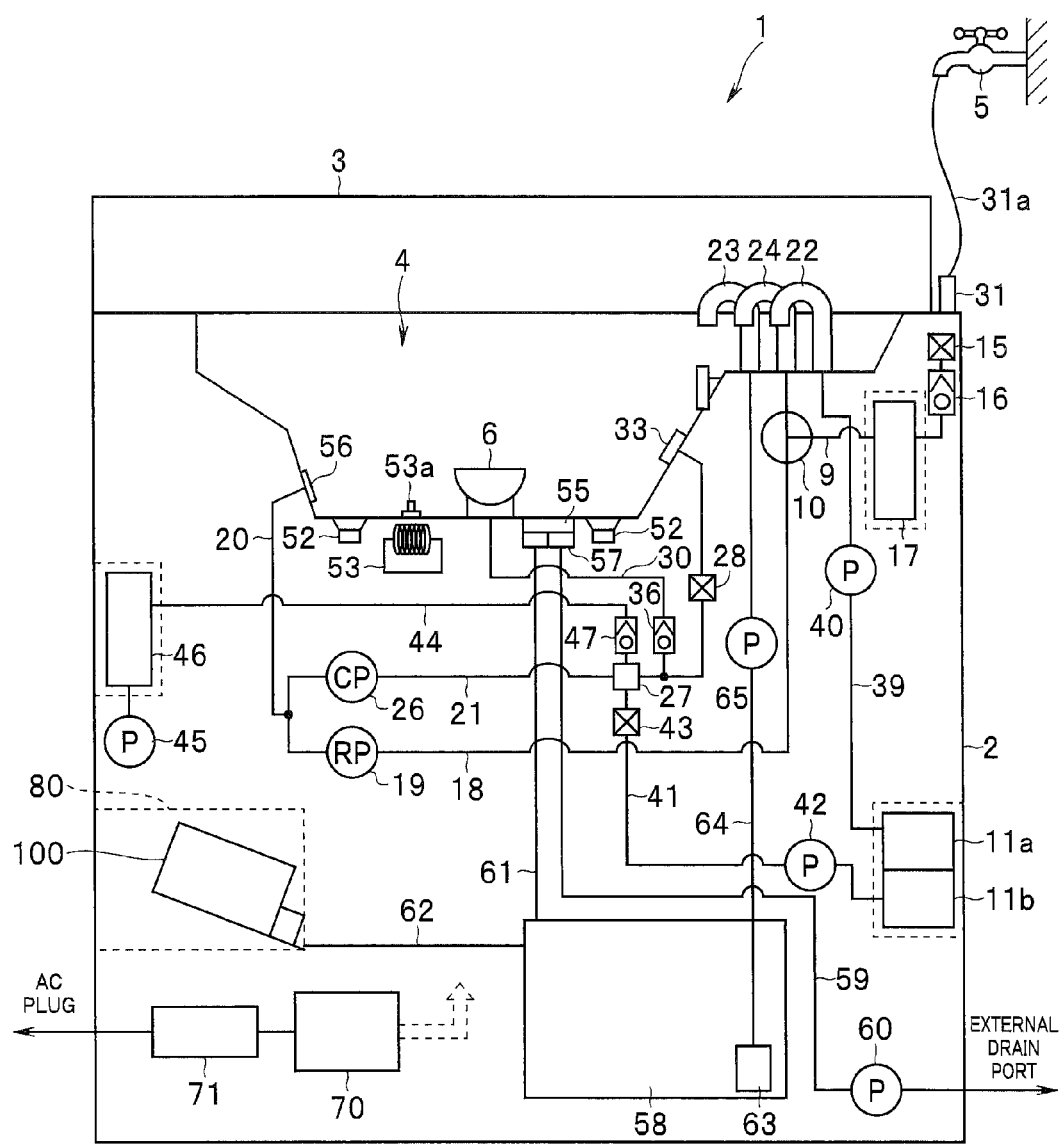
FIG. 2 is an explanatory view illustrating one example of an internal configuration of the endoscope cleaning/disinfecting apparatus in the first embodiment of the present invention.

As illustrated in FIG. 2, the endoscope cleaning/disinfecting apparatus 1 has a configuration in which the water supply hose connection port 31 is connected to one end of the water supply hose 31a, and the other end of the water supply hose 31a is connected to the external tap water faucet 5 to supply tap water. The water supply hose connection port 31 communicates with one end of a water supply tube line 9. The other end of the water supply tube line 9 is connected to a three-way solenoid valve 10. At an intermediate portion in the tube line, a water supply solenoid valve 15, a check valve 16, and a water supply filter 17 are placed in order from the side of the water supply hose connection port 31.

The water supply filter 17 is configured as a cartridge type filtration filter so that the filter can be replaced on a regular basis. The water supply filter 17 removes foreign substances, various germs, and the like, which are contained in the passing tap water.

The three-way solenoid valve 10 is connected to one end of a flow liquid tube line 18 to switch, by using an internal valve, between the water supply tube line 9 and the flow liquid tube line 18 which communicate with a water supply circulation nozzle 24 arranged in a cleaning/disinfecting tank 4 that houses the endoscope. That is, the water supply circulation nozzle 24 communicates with either the water supply tube line 9 or the flow liquid tube line 18 by switching operation of the three-way solenoid valve 10. A flow liquid pump 19 serving as a nonself-priming pump, which can transfer only liquid with an excellent liquid transfer capability, is placed on the other end side of the flow liquid tube line 18.

A circulation port 56 is arranged on a bottom portion side of the cleaning/disinfecting tank 4, and the circulation port 56 is connected to one end of a circulation tube line 20. The other end of the circulation tube line 20 splits into two branches which communicate with the other end of the flow liquid tube line 18 and one end of a channel tube line 21. The other end of the channel tube line 21 communicates with each of air/water feeding/forceps ports 33. Although not illustrated, the other end of the channel tube line 21 also communicates with a forceps uplifting port which is not illustrated.

At an intermediate portion in the channel tube line 21, a channel pump 26, a channel block 27, and a channel solenoid valve 28 are each placed in order from the one end side. At a portion of the channel tube line 21 between the channel block 27 and the channel solenoid valve 28, a case tube line 30 whose one end is connected to a cleaning case 6, is connected thereto at the other end thereof. A relief valve 36 is placed in the case tube line 30. Note that the channel pump 26 is constituted of a self-priming pump which can transport both liquid and gas at higher pressures than the nonself-priming pump.

The cleaning/disinfecting tank 4 is also equipped with a detergent nozzle 22, and the detergent nozzle 22 is connected to one end of a cleaning solution tube line 39. The other end of the cleaning solution tube line 39 is connected to the detergent tank 11a. At an intermediate portion in the cleaning solution tube line 39, a detergent pump 40 is placed which is constituted of a high-pressure self-priming pump for pumping up the cleaning solution from the detergent tank 11a to the cleaning/disinfecting tank 4.

The alcohol tank 11b is connected to one end of an alcohol tube line 41, and the alcohol tube line 41 is connected to the channel block 27 so as to communicate with the channel tube line 21 as specified. In the alcohol tube line 41, an alcohol feed pump 42 is placed which is constituted of a high-pressure self-priming pump for pumping up an alcohol from the alcohol tank 11b to the cleaning/disinfecting tank 4. A solenoid valve 43 is also placed in the alcohol tube line 41.

The channel block 27 is also connected to one end of an air tube line 44 so as to communicate with the channel tube line 21 as specified. The air tube line 44 supplies air from an air pump 45, which is constituted of a self-priming pump that can transport gas. The other end of the air tube line 44 is connected to the air pump 45. A check valve 47 and an air filter 46, which is replaced on the regular basis, are placed at an intermediate position in the air tube line 44.

An drain port 55 is provided on a bottom surface portion of the cleaning/disinfecting tank 4, and a selector valve 57, which is freely opened and closed, is arranged below the drain port 55 for draining a cleaning liquid and the like to an outside or for collecting the disinfecting solution to the chemical tank 58 by switching operation of a valve. The selector valve 57 is connected to the other end of a drain tube line 59 whose one end is connected to and communicates with an unillustrated drain hose connected to an external drain port. In the drain tube line 59, a drain pump 60 constituted of a nonself-priming pump is placed. The selector valve 57 is also connected to one end of a chemical recovery tube line 61, and the other end of the chemical recovery tube line 61 is connected to a chemical tank 58.

The chemical tank 58 is also connected to one end of a chemical supply tube line 62 so as to receive a supply of chemical solution, such as a disinfecting solution, from the chemical bottle 100. The other end of the chemical supply tube line 62 is connected to the chemical bottle insertion passage 80 as specified. The chemical solution injected into the chemical tank 58 through the chemical supply tube line 62 is mixed with dilution water and then used in a disinfecting process.

The chemical tank 58 houses as specified one end portion of a chemical tube line 64, the one end of which is provided with a suction filter 63. The other end of the chemical tube line 64 is connected to a disinfecting solution nozzle 23 arranged in the cleaning/disinfecting tank 4. At an intermediate position in the chemical tube line 64, a chemical pump 65 is placed which is constituted of a high-pressure self-priming pump for pumping up the disinfecting solution from the chemical tank 58 to the cleaning/disinfecting tank 4.

Note that two ultrasound transducers 52 and a heater 53 are arranged in a lower portion of a bottom surface of the cleaning/disinfecting tank 4 for example, for enhancing efficiency of cleaning/disinfecting the endoscope. A temperature detection sensor 53a is also provided in an approximate center of the bottom surface of the cleaning/disinfecting tank 4 for thermoregulation of the heater 53.

The heater 53 is for warming the disinfecting solution, which is stored in the cleaning/disinfecting tank 4 and circulates through the inside of the apparatus, to a specified temperature. Note that the disinfecting solution has a proper temperature at which a maximum disinfection effect can be expected. The disinfecting solution warmed by the heater 53 to the specified temperature that is the proper temperature can effectively disinfect each of the tube lines in the endoscope and the apparatus body 2.

The temperature detection sensor 53a detects the solution temperature of the disinfecting solution which is stored in the cleaning/disinfecting tank 4 and circulates through the inside of the apparatus, and transfers the detection result to a control section 70. A power supply 71 for receiving a power supply from an external AC receptacle, and the control section 70 electrically connected to the power supply 71 are provided inside the endoscope cleaning/disinfecting apparatus 1. The control section 70 receives various signals from the main operation panel 25 and the sub operation panel 13.

The control section 70 controls to drive and stop the heater 53 so as to maintain the disinfecting solution at the specified temperature based on the detection result from the temperature detection sensor 53a, and also executes drive control of components such as each of the pumps and each of the solenoid valves described before.

In the drive control of each of these valves and pumps, the control section 70 includes a water supply tube line disinfecting program, which performs known draining, disinfecting, and rinsing processes in at least the water supply tube line 9, through the circulation tube line 20 and the channel tube line 21. The water supply tube line disinfecting program also performs either a collecting process of collecting at least one of the tap water and the disinfecting solution in the cleaning/disinfecting tank 4 into the chemical tank 58 through the chemical recovery tube line 61, or a draining process of draining at least one of the tap water and the disinfecting solution from the external drain port through the drain tube line 59. The control section 70 also includes an entire tube line disinfecting program for disinfecting the inside of all the tube lines in the endoscope cleaning/disinfecting apparatus 1, and/or an endoscope cleaning/disinfecting program for cleaning/disinfecting an endoscope tube line of the endoscope connected to the port 33 through a tube.

When the endoscope is cleaned/disinfected by the above endoscope cleaning/disinfecting apparatus 1, it is necessary to supply the chemical solution from the chemical bottle 100 (101,102). Next, the chemical tray 81 that houses the chemical bottle 100 will be described. Although the chemical solution is injected from the chemical bottle 100 and stored in the chemical tank 58 in the present embodiment, the chemical solution may be supplied without a use of the chemical tank as long as the chemical solution reaches the cleaning/disinfecting tank 4 in the end.

Figure 3:
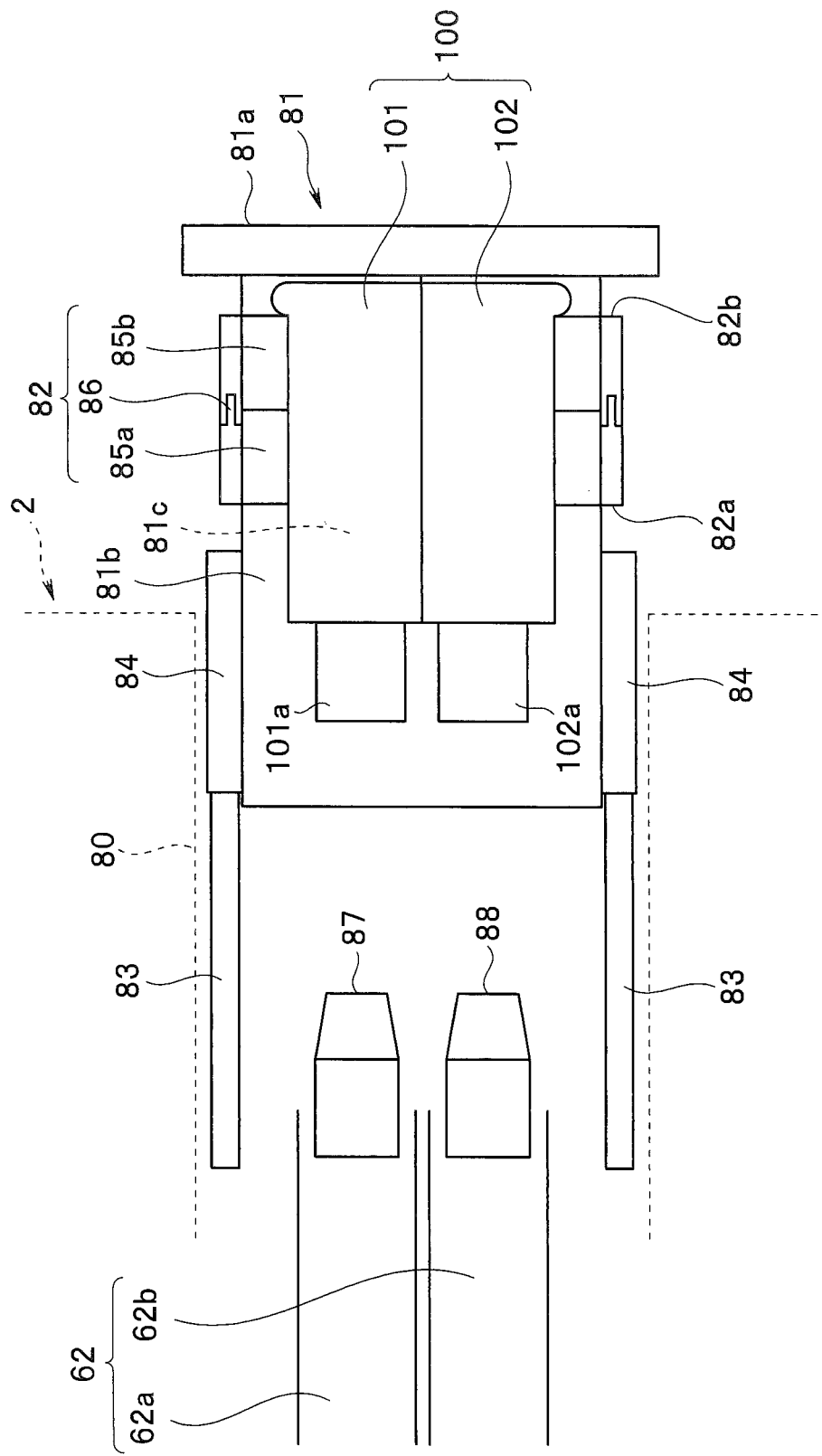
FIG. 3 is an explanatory view illustrating a chemical tray as looked down from an upper surface in the first embodiment of the present invention.

The chemical tray 81 is arranged movably back and forth in the chemical bottle insertion passage 80 which has an opening section on a wall surface of the apparatus body 2 and forms a tunnel for introducing the chemical bottle 100 (101,102). As illustrated in FIG. 3, the chemical tray 81 mainly includes a cover section 81a for sealing the opening of the chemical bottle insertion passage 80, and a bottle set section 81b in which the chemical bottle 100 (101,102) is set and housed. The bottle set section 81b of the chemical tray 81 is equipped with a bottle push-up mechanism 82 for pushing up one end of the chemical bottle 100 (101,102) at a time of chemical injection as described below.

The bottle set section 81b has a mounting surface 81c on which the chemical bottles 101 and 102 are set. The mounting surface 81c is formed horizontal or as an inclined surface with a region on a cover section 81a side being slightly lower, so that the chemical discharge ports of the chemical bottles 101 and 102 are set to face upward or sideward with respect to a gravity direction. Slider members 84 are attached to both side portions of the bottle set section 81b, so that the slider members 84 are engaged with two rail-like guide members 83 arranged inside the chemical bottle insertion passage 80.

The guide members 83 form a slider rail mechanism in unison with the slider members 84 to achieve smooth back-and-forth movement of the chemical tray 81, and functions as a guide section that restricts an advancing direction of the bottle set section 81b and thereby guides the bottle set section 81b to move back and forth in a portion between a first position and a second position described later. Although movement from the first position to the second position is in a transverse direction with respect to the gravity direction in the present embodiment, the movement may be in a lengthwise direction instead of the transverse direction. The slider members 84 may be omitted, and both the side portions of the bottle set section 81b themselves may directly be engaged with the guide members 83 to restrict the back-and-forth movement.

The bottle push-up mechanism 82 is placed on a cover section 81a side of the bottle set section 81b, and is configured as a hinge having two plate-like push-up members 85a and 85b placed from front to back in a direction approximately orthogonal to a back-and-forth movement direction of the bottle set section 81b and a joint section 86 pivotably joining these push-up members 85a and 85b. A free end 82a, which is an end portion of the bottle push-up mechanism 82 that faces the guide member 83, is placed to be a free end which can freely move back and forth. A fixed end 82b, which is an end portion of the bottle push-up mechanism 82 on a cover section 81a side, may be fixed to the cover section 81a or the bottle set section 81b so that its back-and-forth movement is restricted, or the back-and-forth movement may be restricted when the fixed end 82b collides with the cover section 81a.

The chemical bottles 101 and 102 are loaded on the push-up members 85a and 85b, and are set in the bottle set section 81b. Plug sections 101a and 102a, which are end portions on a distal end side of the chemical bottles 101 and 102, serve as chemical discharge sections. The plug sections 101a and 102a each have a sealing member for sealing an internal chemical solution, which is made of a thin film and the like that can be broken by a specified load.

In the present embodiment, a first cutter section 87 and a second cutter section 88 are arranged in the chemical bottle insertion passage 80 of the apparatus body 2 as unsealing sections for unsealing the plug sections 101a and 102a of the chemical bottles 101 and 102 to form chemical discharge ports. The first cutter section 87 and the second cutter section 88 are each formed to have a sharp distal end portion. These first cutter sections 87 and the second cutter sections 88 are each connected to tube lines 62a and 62b, which constitute the above-described chemical supply tube line 62. Note that the unsealing sections are not limited to cutters. For example, the chemical discharge port may be formed in the bottle with a laser and water pressure, or a connector-type unsealing section may also be used which forms a chemical discharge port by twisting a cap-like bottle cover section.

Figure 4:
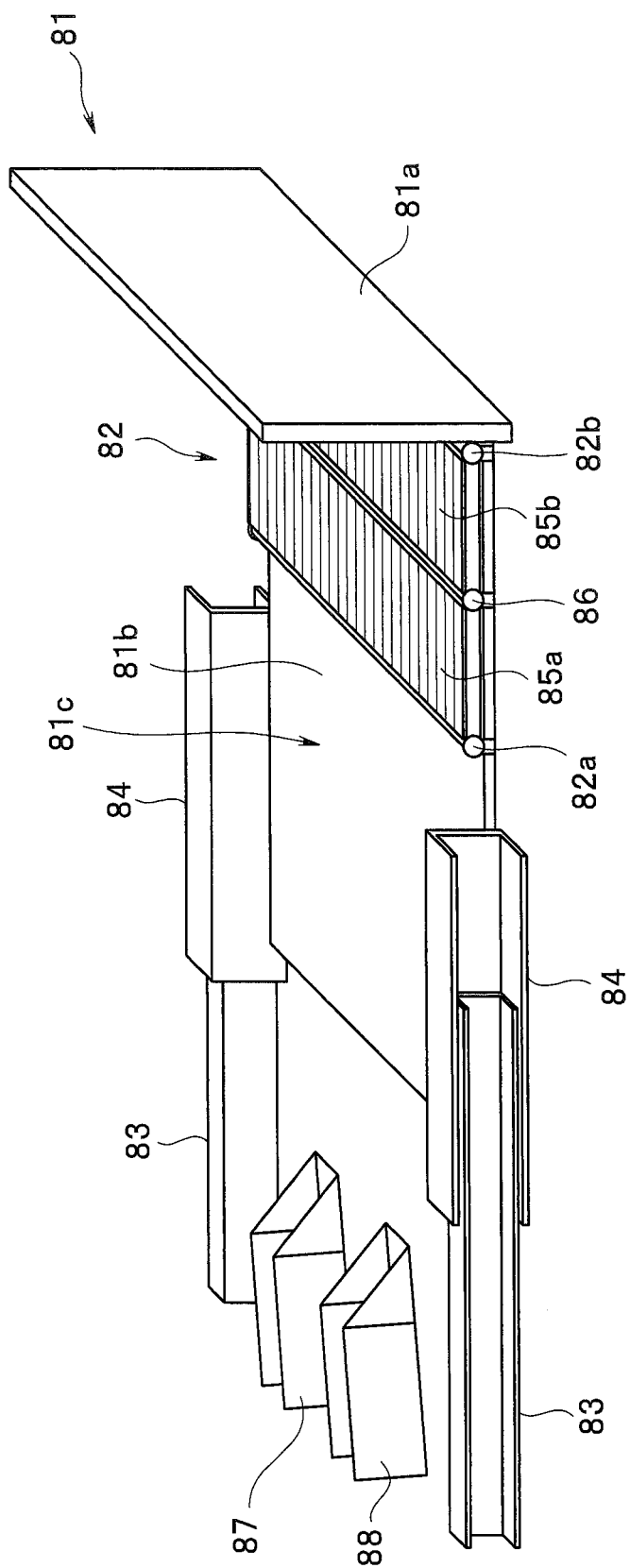
FIG. 4 is a perspective view illustrating a state in which the chemical tray is drawn out and a chemical bottle is not set in the first embodiment of the present invention.

As illustrated in FIG. 4, when the chemical tray 81 is drawn out from the apparatus body 2 to a first position that is for setting and extracting the chemical bottles 101 and 102, the bottle push-up mechanism 82 is expanded so that two push-up members 85a and 85b constitute one plane on the bottle set section 81b. When the chemical tray 81 is pushed forward from this first position, an advancing direction of the bottle set section 81b is restricted by the guide members 83 at an apparatus body 2 side and by the slider members 84 of the bottle set section 81b. As a result, the bottle set section 81b linearly moves inside the chemical bottle insertion passage 80.

Figure 5:
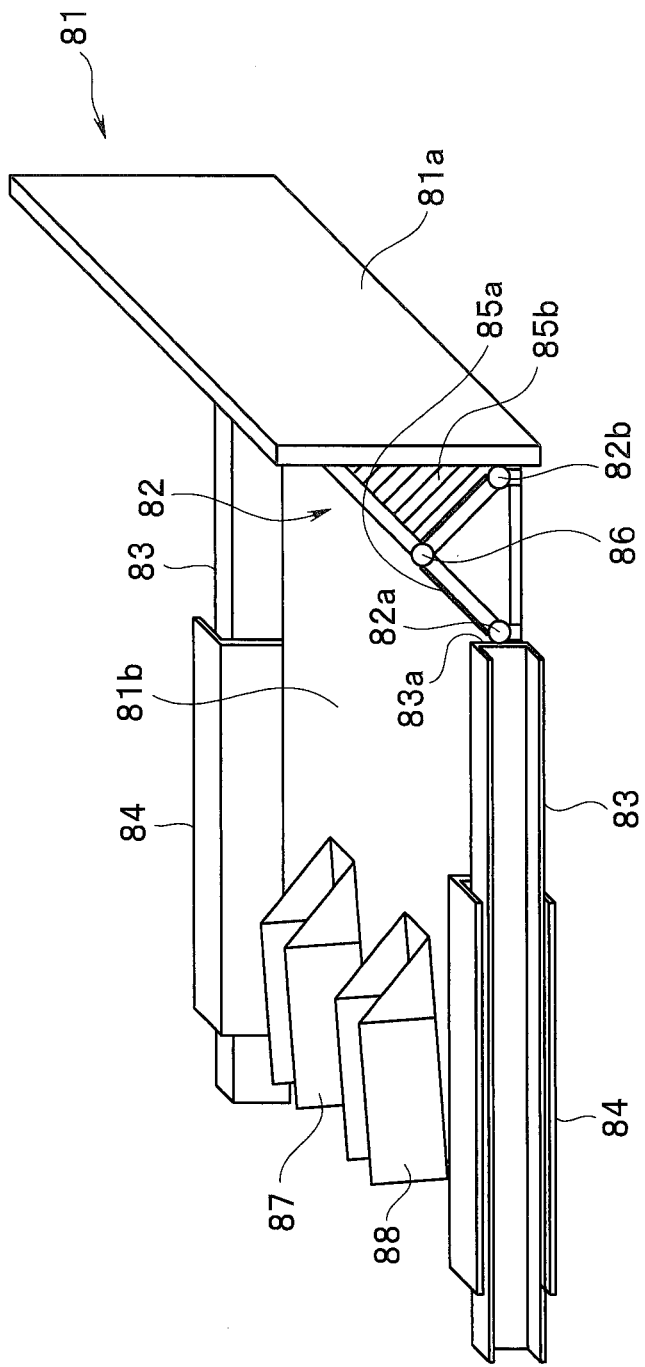
FIG. 5 is a perspective view illustrating a state in which a bottle push-up mechanism is operated from the state of FIG. 4 in the first embodiment of the present invention.

In this case, when the end portion 82a on a distal end side of the bottle push-up mechanism 82 collides with a distal end portion 83a of the guide member 83 and further pushes the chemical tray 81 forward, both ends of the bottle push-up mechanism 82 come close to each other and the joint section 86 at a center is pushed upward as illustrated in FIG. 5. As the joint section 86 moves upward, the push-up members 85a and 85b in the expanded state are folded into a ridge shape and are pushed upward.

Figure 6:
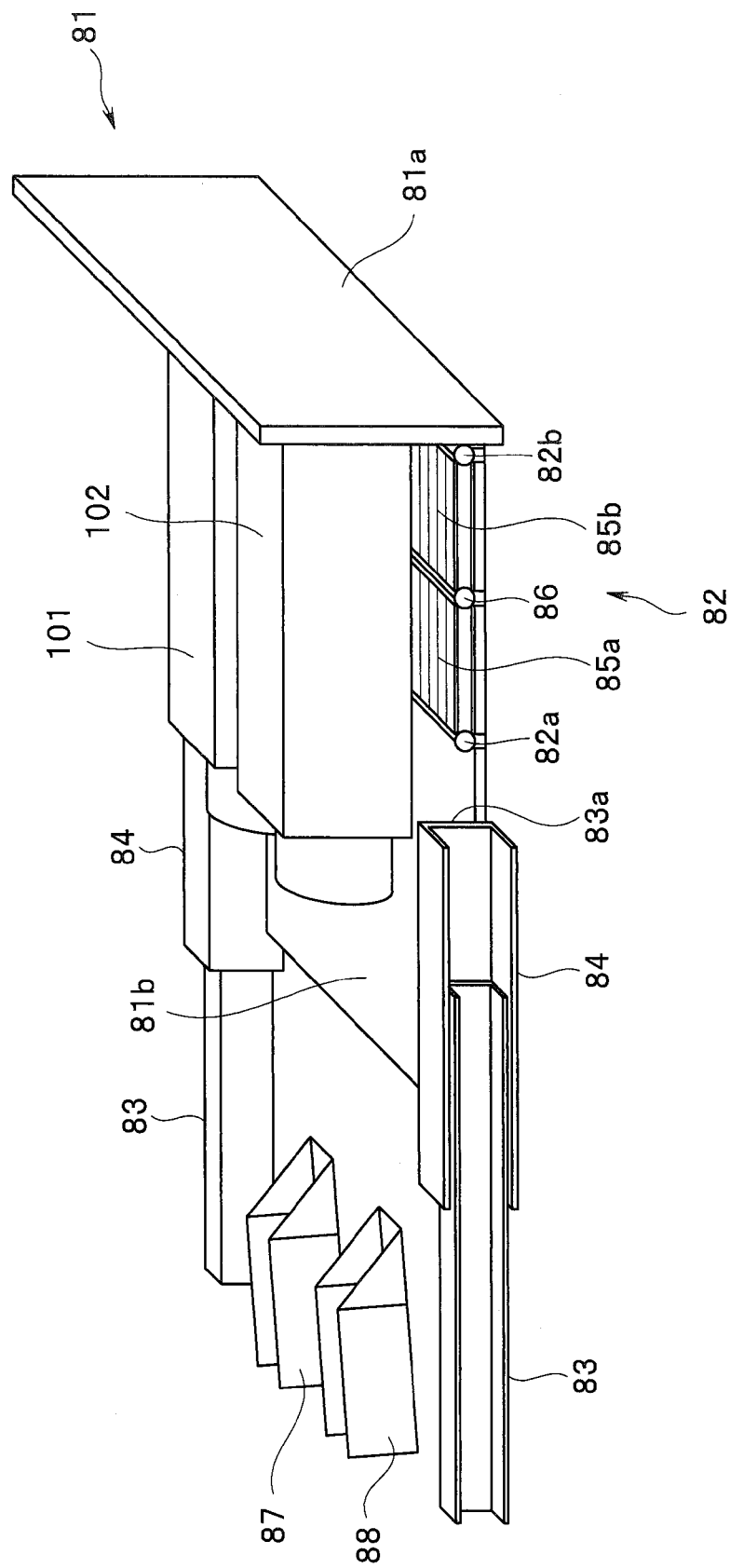
FIG. 6 is a perspective view illustrating a state in which the chemical bottle is set in FIG. 4 in the first embodiment of the present invention.
Figure 7:
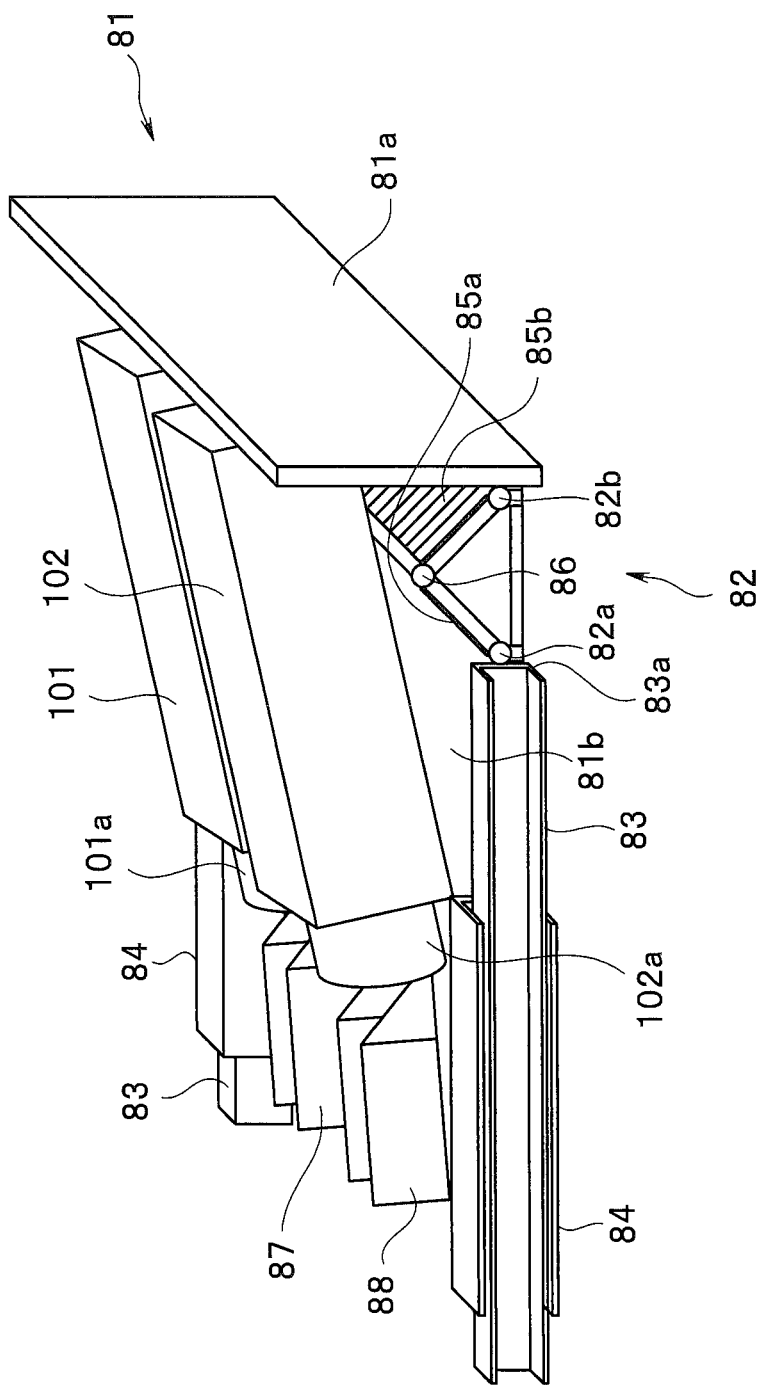
FIG. 7 is a perspective view illustrating a state in which the bottle push-up mechanism is operated from the state of FIG. 6 in the first embodiment of the present invention.

Therefore, when the chemical tray 81 is pushed forward from the state of FIG. 6 where the chemical bottles 101 and 102 are set, the chemical tray 81 is put in a second position illustrated in FIG. 7. At the second position, the cutter sections 87 and 88 are butted against the plug sections 101a and 102a of the chemical bottles 101 and 102 in the state that a rear end side of the chemical bottles 101 and 102 is pushed up by the push-up members 85a and 85b so that the plug sections 101a and 102a of the chemical bottles 101 and 102 face downward in the gravity direction. Consequently, the sealing members are broken and the internal chemical solutions flow out by gravity.

That is, when the guide members 83 including the distal end portions 83a are used as a first push-up section fixed to the chemical bottle insertion passage 80, the bottle push-up mechanism 82 functions as a second push-up section. That is, the bottle push-up mechanism 82 collides with the distal end portion 83a that is the first push-up section when the bottle set section 81b is caused to advance from the first position to the second position. The bottle push-up mechanism 82 receives force upon the collision and transfers the force to the chemical bottles 101 and 102 to push up end portions (first end portions) of a bottom portion side of the chemical bottles 101 and 102, so that the plug sections 101a and 102a face downward in the gravity direction. Note that, at the second position, the opening of the chemical bottle insertion passage 80 is in the state of being sealed by the cover section 81a.

That is, since the first push-up sections 83 functions as an obstacle, the chemical bottle 100 is prevented from advancing toward the unsealing section 89 while keeping the state of being inclined as in the first position.

Hereinafter, a series of operations from setting the bottles on the chemical tray 81 to collection of the bottles after chemical injection will be described with reference to FIGS. 8 to 12. Note that in the following description, the chemical bottles 101 and 102 are described as a chemical bottle 100, and the cutter sections 87 and 88 for unplugging are described as a cutter section 89.

Figure 8:
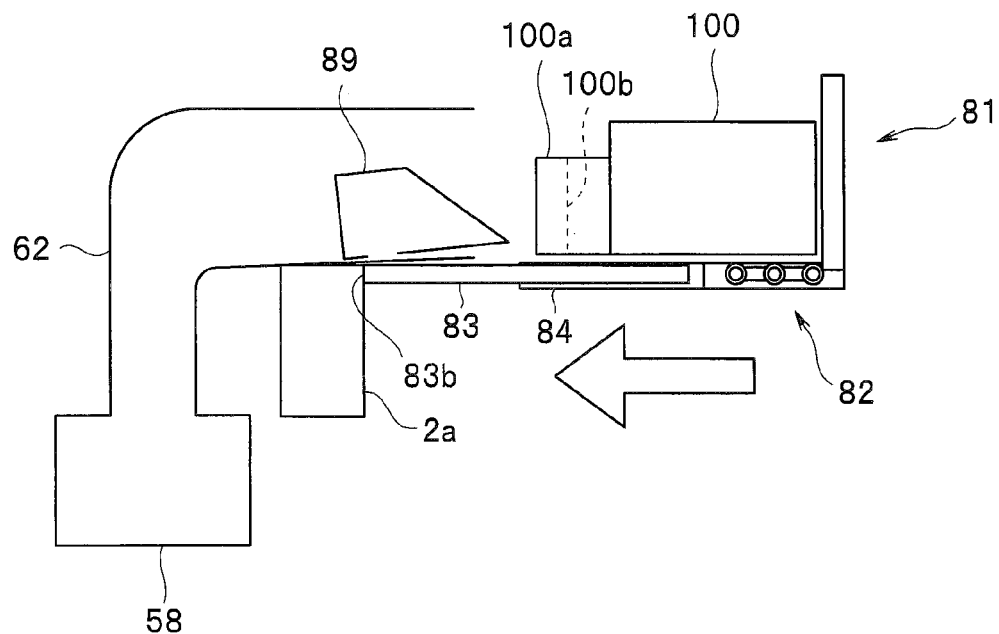
FIG. 8 is an explanatory view illustrating a state in which the chemical bottle is set in the first embodiment of the present invention.

First, as illustrated in FIG. 8, in the state where the chemical tray 81 is drawn out from the apparatus body 2, an unused chemical bottle 100 is set in the bottle set section 81b. At this time, the chemical bottle 100 is set in a horizontal state or set so that a plug section 100a of the chemical bottle 100 faces slightly upward with respect to the gravity direction, depending on a shape of a loading surface of the bottle set section 81b.

Note that a dashed line in the plug section 100a represents a sealing member 100b for sealing the internal chemical solution. Rear end portions 83b of the guide members 83 arranged in the apparatus body 2 are brought into contact with and fixed to a contact section 2a of the apparatus body 2.

Figure 9:
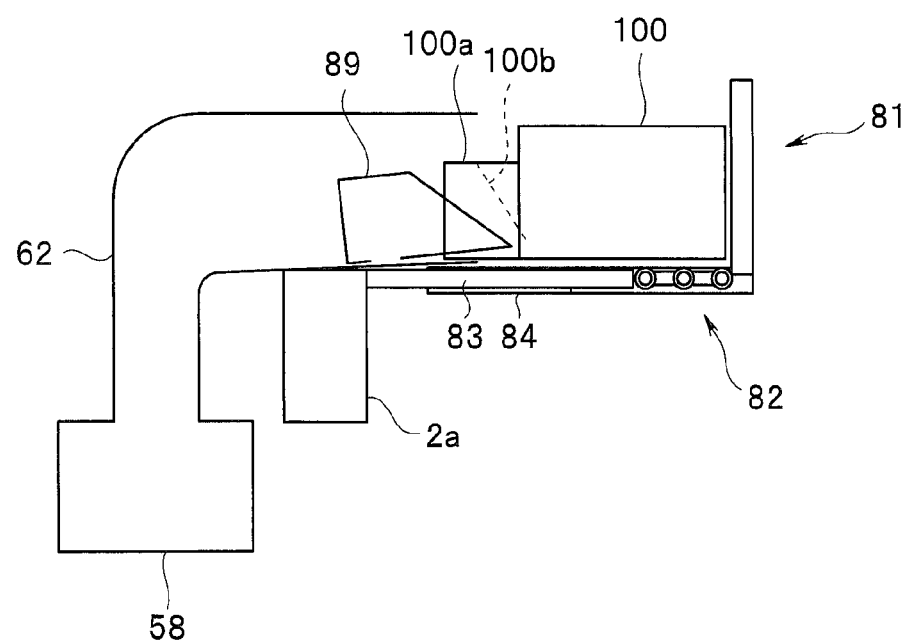
FIG. 9 is an explanatory view illustrating unplugging of the chemical bottle in the first embodiment of the present invention.

When the chemical bottle 100 is set and then the chemical tray 81 is pushed in an arrow direction in the drawing, the slider members 84 are guided by the guide members 83, so that the chemical tray 81 moves. Then, as illustrated in FIG. 9, the cutter section 89 is butted against the plug section 100a of the chemical bottle 100.

Figure 10:
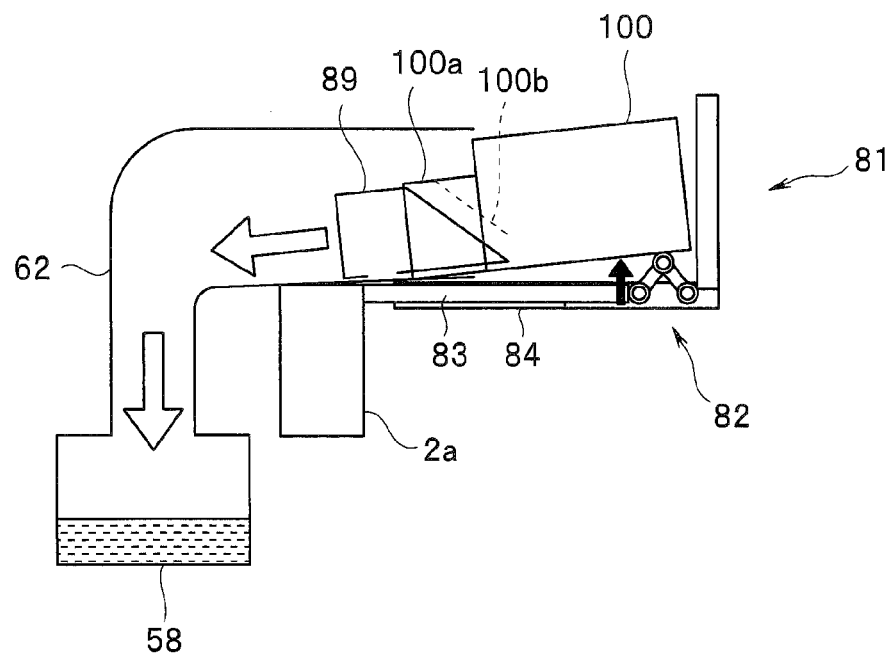
FIG. 10 is an explanatory view illustrating injection of the chemical solution in the first embodiment of the present invention.
Figure 11:
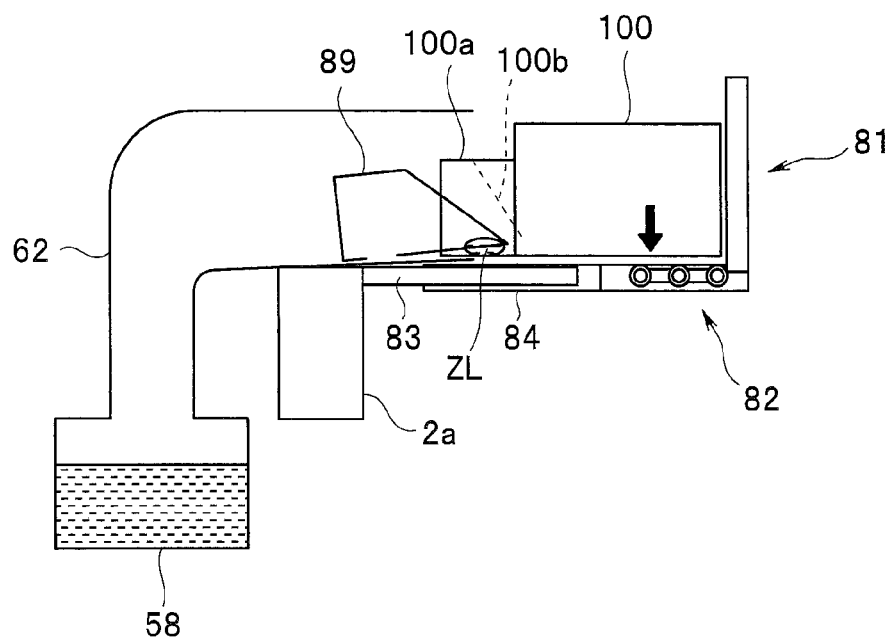
FIG. 11 is an explanatory view illustrating a drawing-out operation 1 of the chemical bottle in the first embodiment of the present invention.

In this case, at a moment of unplugging or immediately before unplugging, the bottle push-up mechanism 82 operates in conjunction with guiding by the guide member 83, so that a rear portion of the chemical bottle 100 is pushed up by the push-up members 85a and 85b as illustrated in FIG. 10. As a result, the chemical bottle 100 inclines so that the plug section 100a faces downward in the gravity direction, and the internal chemical solution flows out by gravity and are injected into the chemical tank 58 from the chemical supply tube line 62.

Then, once the chemical injection to the chemical tank 58 is completed, the chemical tray 81 is drawn out for collecting and replacing the chemical bottle 100. As a result, as indicated with an arrow in FIG. 11, the push-up members 85a and 85b of the bottle push-up mechanism 82 go down from a standing state and return to an initial planar state. In connection with this, the chemical bottle 100 returns to an original set position in which the chemical bottle 100 is in a horizontal state or the plug section 100a faces slightly upward with respect to the gravity direction.

Figure 12:
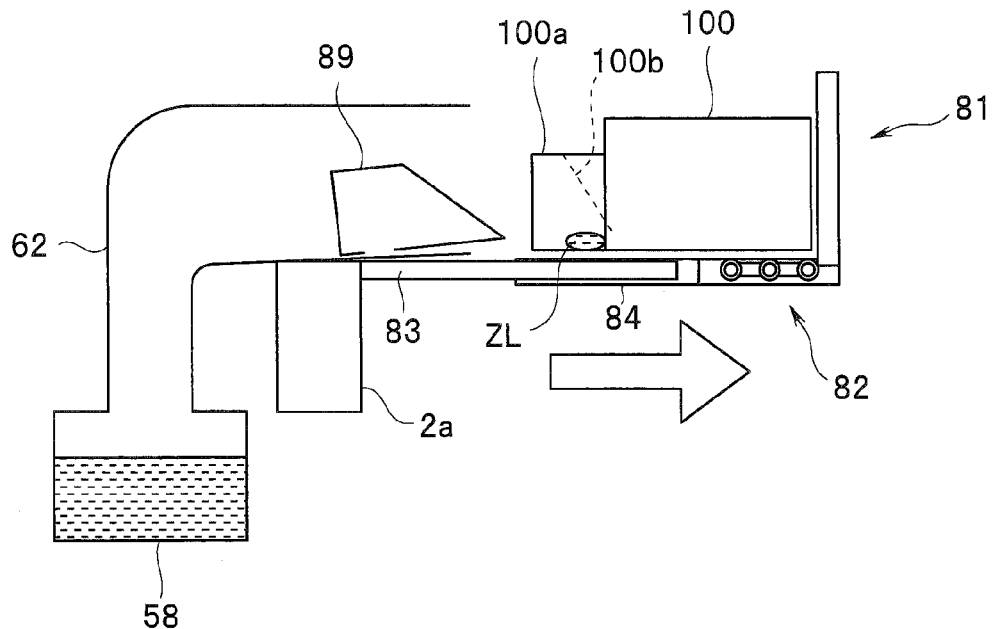
FIG. 12 is an explanatory view illustrating a drawing-out operation 2 of the chemical bottle in the first embodiment of the present invention.

Therefore, since the chemical tray 81 is drawn out while the chemical bottle 100 is retained in the original set position, in which the chemical bottle 100 is in the horizontal state or the plug section 100a faces slightly upward with respect to the gravity direction, a chemical solution ZL remaining in the chemical bottle 100 is prevented from flowing to the outside by gravity even when the plug section 100a of the chemical bottle 100 is distanced from the cutter section 89 as illustrated in FIG. 12.

Thus, in the present embodiment, the chemical bottle 100 is so set that the plug section 101a of the chemical bottle 100 is in a horizontal position or faces slightly upward from the horizontal position in the initial state. At a time of unplugging, the rear portion of the chemical bottle 100 is pushed up by the bottle push-up mechanism 82 so that the plug section 101a is positioned downward in the gravity direction to enable the chemical solution to gravitationally flow out to the outside. When the bottle is replaced, the bottle position is returned to the initial state in which the plug section 101a is in a horizontal position or faces slightly upward from the horizontal position.

That is, in the past, when the bottle position was returned to the initial set position, the plug section was slightly lower than the horizontal position and thereby a residual liquid in the bottle possibly dripped to the outside. However, in the endoscope cleaning/disinfecting apparatus 1 in the present embodiment, when the chemical bottle is drawn out after chemical injection is completed, the chemical bottle is returned to the initial state in which the plug section 101a is in a horizontal position or faces slightly upward from the horizontal position. This makes it possible to prevent the residual liquid from dripping down. Moreover, since the opening of the chemical bottle insertion passage 80 in the apparatus body 2 is sealed by the cover section 81a of the chemical tray 81 at a time of chemical injection, it becomes possible to prevent a volatile constituent from leaking out of the apparatus body 2 even in the case of using a highly volatile chemical solution such as peracetic acid.

Second Embodiment

Next, a second embodiment of the present invention will be described. In the second embodiment, the bottle push-up mechanism 82 is modified. Hereinafter, difference from the first embodiment will be described.

Figure 13:
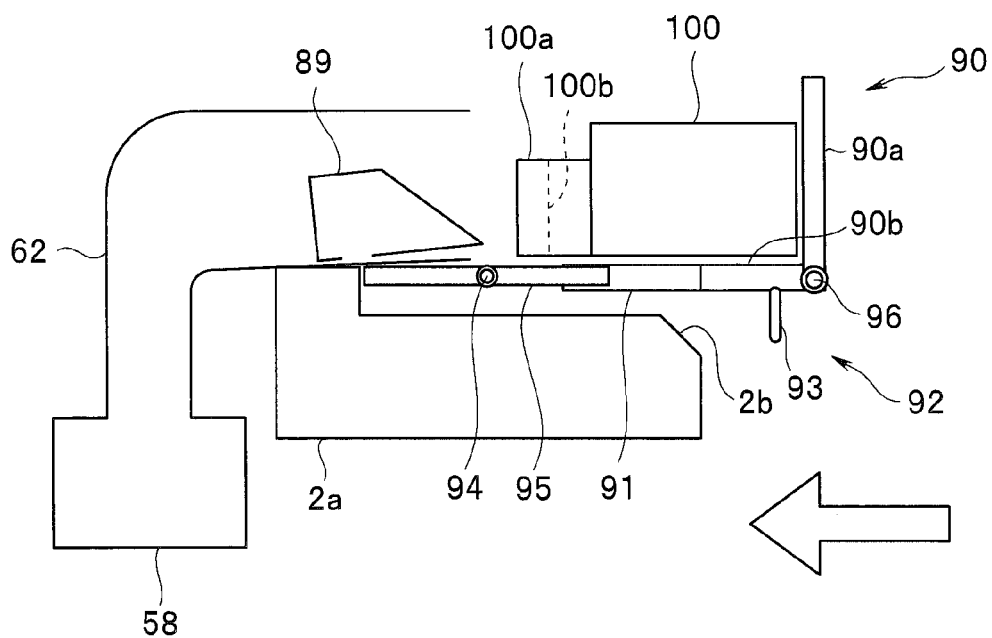
FIG. 13 is an explanatory view of a chemical tray in a second embodiment of the present invention.

As illustrated in FIG. 13, a chemical tray 90 in the second embodiment includes a cover section 90a, a bottle set section 90b, and a slider member 91 similar to those in the first embodiment, while the bottle push-up mechanism 82 of the first embodiment is replaced with a bottle push-up mechanism 92 serving as a second push-up section. The bottle push-up mechanism 92 mainly includes a push-up member 93 which is fixed to a region below the bottle set section 90b and in a vicinity of the cover section 90a so as to protrude downward in the gravity direction.

The apparatus body 2 side is also slightly modified from the first embodiment in accordance with the push-up member 93 of the bottle push-up mechanism 92. More specifically, a receiving section 2b is provided as a first push-up section on a lower surface side of an entrance of the opening section of the apparatus body 2 that houses the chemical tray 90. The receiving section 2b has an inclined surface which comes into contact with and are ridden on by a lower end side of the push-up member 93 when the chemical tray 90 is pushed forward. Although the receiving section 2b serving as the first push-up section is formed in the contact section 2a in FIG. 13, the present invention is not limited to this configuration. In the second embodiment, it is not essential that the guide member 95 is configured to come into contact with the contact section 2a.

Note that the push-up member 93 may be configured as part of the cover section 90a, which is extended below the bottle set section 90b to seal the opening of the bottle insertion passage. This makes it possible to seal the bottle insertion passage and to thereby prevent a volatilized chemical solution from leaking out of the bottle insertion passage.

The guide members 83 of the apparatus body 2, which constitute a slider rail mechanism in unison with the slider members 91, are modified into guide members 95 each equipped with a hinge 94 at an approximately central portion. The guide members 95 are therefore configured foldably via the hinges 95. Note that in the chemical tray 90, the cover section 90a and the bottle set section 90b are also coupled through a hinge 96, so that angles of the cover section 90a and the bottle set section 90b are variable.

In the initial state in FIG. 13 in which the chemical tray 90 is drawn out and the chemical bottle 100 is set, the push-up member 93 of the bottle push-up mechanism 92 is distanced from the receiving section 2b of the apparatus body 2. In this state, the chemical bottle 100 is retained in an initial state in which the plug section 100a is in a horizontal position or faces slightly upward from the horizontal position.

Figure 14:
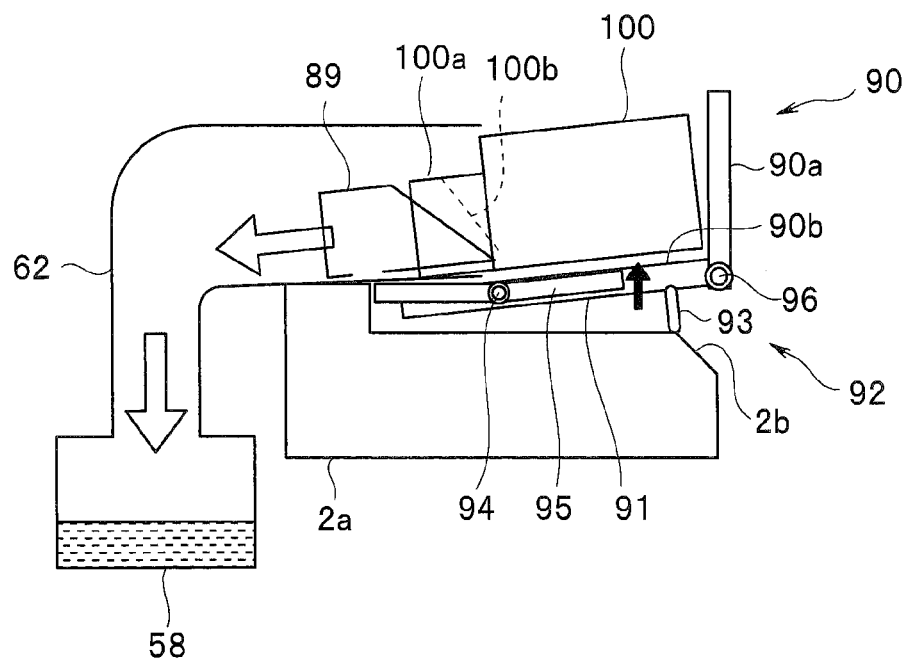
FIG. 14 is an explanatory view illustrating a state in which the chemical bottle is unplugged in the second embodiment of the present invention.

When the chemical tray 90 is pushed forward from the initial state, a lower end side of the push-up member 93 of the bottle push-up mechanism 92 comes into contact with the receiving section 2b of the apparatus body 2 and rides on the inclined surface of the receiving section 2b, so that the bottle set section 90b is pushed up as illustrated in FIG. 14. Consequently, the rear portion of the chemical bottle 100 is pushed up, and the plug section 100a is unsealed by the cutter section 89 in the inclined state of facing downward in gravity direction. Accordingly, the internal chemical solution flows out by gravity, and is injected into the chemical tank 58 from the chemical supply tube line 62.

That is, in the second embodiment, the bottle push-up mechanism 92 having the push-up member 93 is used as a second push-up section, and the receiving section 2b is used as a first push-up section placed below the second push-up section in the gravity direction. When the second push-up section rides on the first push-up section and thereby pushes up the bottle set section 90b, the chemical bottle 100 housed in the bottle set section 90b is inclined.

Note that in this case, the guide members 83 of the apparatus body 2 fold via the hinges 94 for smooth inclination of the bottle set section 90b. The cover section 90a is also slightly expanded with respect to the bottle set section 90b through the hinge 96 so as to be approximately flush with a wall surface of the apparatus body 2.

When the chemical tray 90 is drawn out after completion of chemical injection, the push-up member 93 of the bottle push-up mechanism 92 is distanced from the receiving section 2b, and is returned to the initial state of FIG. 13. That is, the chemical bottle 100 returns to the original set position in which the chemical bottle is in a horizontal state or the plug section 100a faces slightly upward with respect to the gravity direction.

In the second embodiment, when the chemical bottle is replaced after completion of chemical injection as in the first embodiment, the chemical bottle is returned to the original set position, in which the chemical bottle is in the horizontal state or the plug section faces upward with respect to the gravity direction. This prevents the chemical solution remaining in the chemical bottle from flowing to the outside by gravity. Even in the case of a chemical solution with a high chemical volatility, it becomes possible to prevent a volatile constituent from leaking out of the apparatus body at a time of chemical injection.

Figure 15:
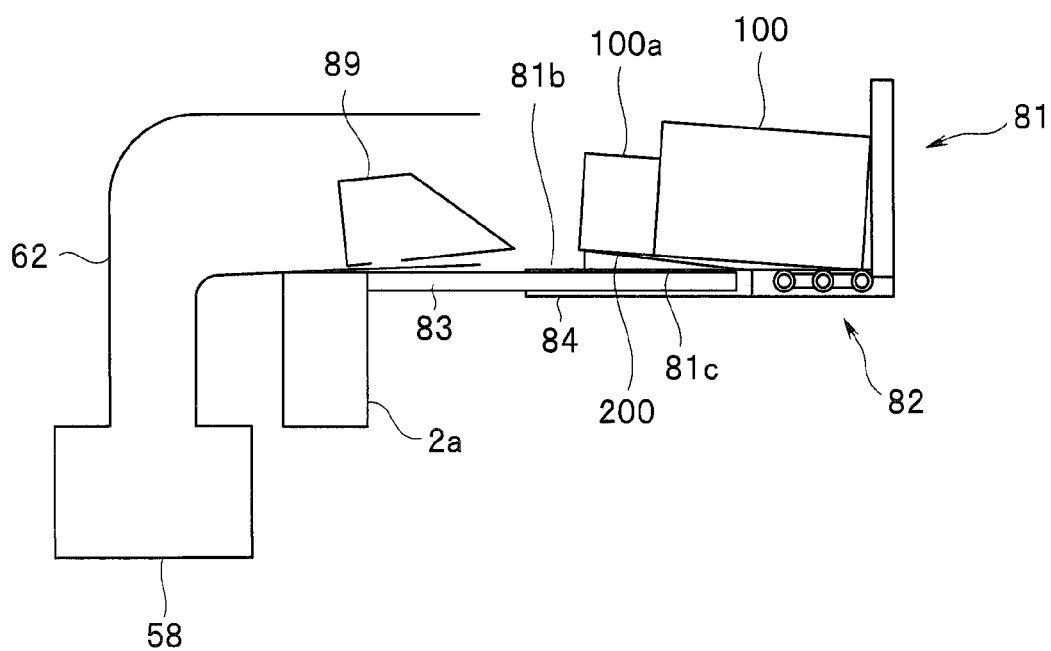
FIG. 15 is an explanatory view illustrating an example of an inclined surface provided on a mounting surface of the chemical bottle.

Note that, as illustrated in FIG. 15, an inclined surface 200 may be provided on the chemical bottle mounting surface 81c of the bottle set section 81b so that the discharge port faces upward in the gravity direction when the chemical bottle 100 is in the first position.

What is claimed is:

1. An endoscope cleaning/disinfecting apparatus for cleaning/disinfecting an endoscope, comprising:
    a bottle insertion passage having an opening section on a wall surface of an apparatus body and for introducing a chemical bottle with a chemical solution enclosed therein;
    an unsealing section placed in the bottle insertion passage for unsealing a chemical discharge section of the chemical bottle to form a chemical discharge port in the chemical bottle;
    a bottle set section placed movably back and forth inside the bottle insertion passage for housing the chemical bottle so that the chemical discharge section faces upward or sideward with respect to a gravity direction;
    a guide section placed in the bottle insertion passage for restricting an advancing direction of the bottle set section so that the bottle set section moves linearly back and forth in a portion between the first position and the second position, assuming that a position of the bottle set section for laying the chemical bottle on the bottle set section and for extracting the chemical bottle from the bottle set section is defined as a first position, and a position of the bottle set section for unsealing the chemical bottle with the unsealing section is defined as the second position;
    a first push-up section serving as an obstacle fixed to the bottle insertion passage; and
    a second push-up section placed in the bottle set section for transferring force to the chemical bottle to push up a first end portion of the chemical bottle so that the chemical discharge port faces downward in the gravity direction, the force being received upon collision with the first push-up section when the bottle set section is caused to advance from the first position to the second position.

2. The endoscope cleaning/disinfecting apparatus according to claim 1, wherein
    the second push-up section is a hinge having a free end, a fixed end, and a joint section placed between the free end and the fixed end, and
    when the free end collides with the first push-up section, the free end and the fixed end come close to each other, and the joint section folds in a direction in which the chemical bottle is placed, and pushes up the chemical bottle.

3. The endoscope cleaning/disinfecting apparatus according to claim 1, wherein
    the first push-up section is placed below the second push-up section in the gravity direction,
    the second push-up section is fixed so as to protrude downward in the gravity direction from a bottom surface of the bottle set section, and
    the second push-up section pushes up the bottle set section by riding on the first push-up section and inclines the chemical bottle housed in the bottle set section.

4. The endoscope cleaning/disinfecting apparatus according to claim 1, wherein
    the bottle set section has an inclined surface on a mounting surface of the chemical bottle so that the chemical discharge port of the chemical bottle mounted at the first position faces upward with respect to the gravity direction.

5. The endoscope cleaning/disinfecting apparatus according to claim 1, further comprising a cover section connected to the bottle set section for closing the opening of the bottle insertion passage when the bottle set section is positioned at a second position.

* * * * *